United States Patent [19]

Boyden, Jr. et al.

[11] 3,990,437
[45] Nov. 9, 1976

[54] ARTICLE AND METHOD OF FORMING A SUPPORT STRUCTURE

[76] Inventors: John S. Boyden, Jr., 1942 Yalecrest Ave.; William W. Epstein, 1193 S. 1900 East, both of Salt Lake City, Utah 84108; Paul W. Boyden, 1474 Laird Ave., Salt Lake City, Utah 84105

[22] Filed: Sept. 26, 1974

[21] Appl. No.: 509,452

[52] U.S. Cl. .................... 128/90; 204/159.14; 204/159.23; 264/22; 264/171; 264/236; 428/253; 428/398; 428/913
[51] Int. Cl.[2] ............... A61F 5/04; A61F 13/06
[58] Field of Search ............. 264/171, 182, 184, 22, 264/236; 128/90; 161/75, 76, 88, 89, 175; 428/229, 230, 245, 253, 262, 265, 398, 913; 204/159.14, 159.23

[56] References Cited
UNITED STATES PATENTS

| | | | |
|---|---|---|---|
| 2,367,660 | 1/1945 | Agre | 128/90 |
| 3,329,557 | 7/1967 | Magat et al. | 161/175 |
| 3,403,070 | 9/1968 | Lewis | 161/175 |
| 3,421,501 | 1/1969 | Beightol | 428/913 |
| 3,458,615 | 7/1969 | Bragaw | 161/175 |
| 3,516,903 | 6/1970 | Jones et al. | 161/175 |
| 3,556,635 | 1/1971 | Schrenh et al. | 264/171 |

*Primary Examiner*—James J. Bell
*Attorney, Agent, or Firm*—Hibben, Noyes & Bicknell

[57] ABSTRACT

The article used and the method of forming a support structure, such as an orthopedic cast, comprising interlacing one or more flexible, pliable filaments having a photopolymerizable material enclosed entirely within the interior of the filaments so as to form a pliable fabric article which can be readily conformed to the surface with which it is in contact and exposing the fabric article to a source of wave energy, such as ultra-violet light, which effects polymerization of the material within the filament and transforming the fabric into a rigid structure entirely by means of the mechanical interlock formed between the filaments; thereby forming a rigid support structure without the application of a malodorous, sticky or powdered stiffening or bonding agent to the outer surface of the filaments or fabric.

14 Claims, 7 Drawing Figures

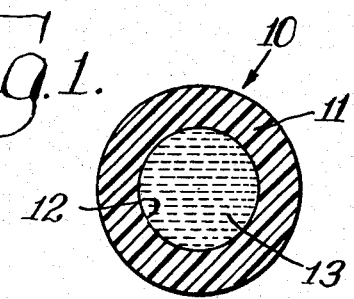
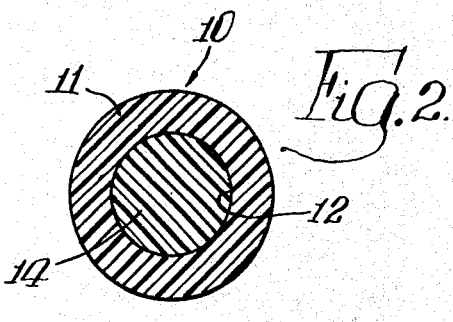
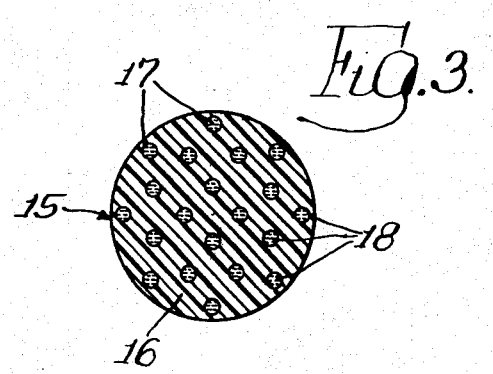
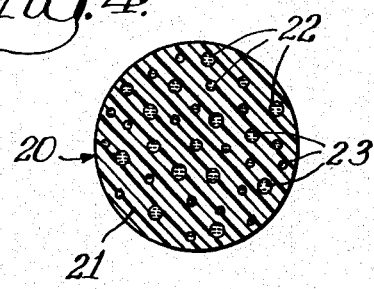
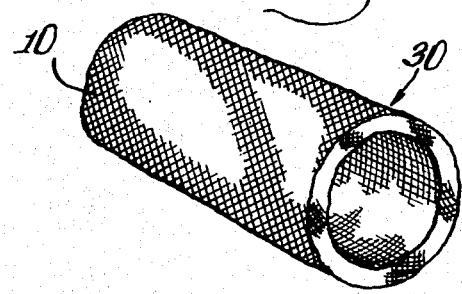
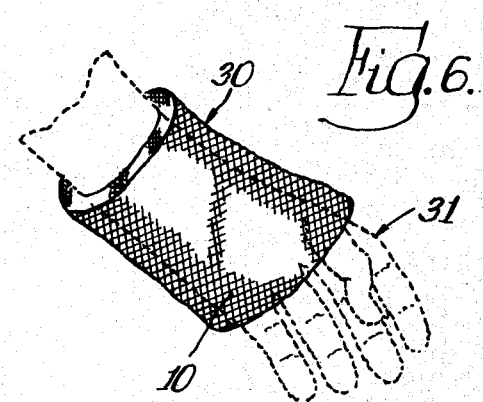
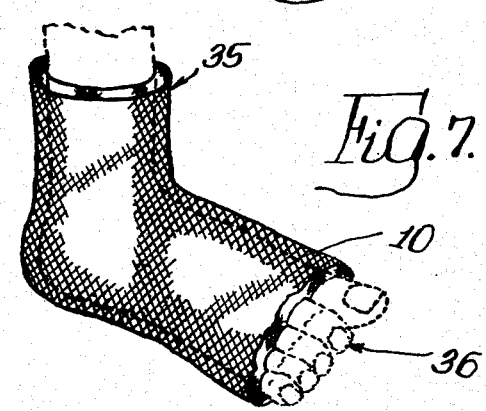

ARTICLE AND METHOD OF FORMING A SUPPORT STRUCTURE

The present invention relates generally to an improved method and means for maintaining an element or structure rigid, and more particularly to a novel method and means for providing an improved rigid supporting structure, such as an orthopedic cast, which can be conveniently used where conditions require that the supporting structure be pliable during installation and rigid during use.

It has heretofore been found advantageous to use plastic materials for making supporting structures, such as orthopedic casts, because the plastic materials are lighter, more easily applied and more resistant to water than conventional plaster casts. One method of making plastic orthopedic casts is described in U.S. Pat. No. 3,421,501, wherein a woven or non-woven fabric has on the surface of the fibers forming the fabric and in the space between the fibers an ultra-violet curable polymer, such as a polymerizable organic composition containing a photosensitizing polymerization initiator which is activated by exposure to ultra-violet light, and after wrapping the fabric about a patient's fractured limb, the impregnated fabric is exposed to ultra-violet light to effect polymerization of the organic material and formation of a rigid light weight plastic cast. Other materials and methods for impregnating a fabric and forming a plastic orthopedic cast are described in U.S. Pat. Nos. 3,618,599, 3,613,675 and 2,812,570.

Plastic orthopedic casts formed in situ in accordance with the foregoing disclosures have many advantages over a conventional plaster cast. However, forming orthopedic plastic casts from fabrics which have the interstices thereof impregnated with a plastic material in accordance with the prior art has many objectionable features. For example, these prior art impregnated fabrics either have an objectionable odor, are tacky during application, or require the use of hand cream or jelly to facilitate proper smoothing and blending of the layers of impregnated fabric. And, it is desirable to use rubber gloves when forming an orthopedic cast from such impregnated fabrics. It is also possible for the impregnating plastic material to come into direct contact with the body of the patient or the attendant, causing irritation or other deleterious effects unless special precautions are taken to maintain the impregnated fabric out of contact with the exposed body surfaces. And, the polymerizable material which is impregnated in the interstices of the fabric may deteriorate or stiffen during storage, if exposed to the surrounding atmosphere unless special precautions and packaging procedures are maintained. Fabrics which are impregnated with the polymerizable material are limited in the amount of handling and molding which can be applied thereto during storage and application. Also, the amount of air circulation or breathing of prior art plastic casts is limited, because a significant proportion of the openings in the fabric are permanently blocked or reduced in size by the impregnated polymerizable plastic material.

Accordingly, it is an object of the present invention to provide a method and means for providing an improved flexible, pliable or elastic element which is adapted to be readily manipulated and shaped into a desired configuration and thereafter made rigid by exposing to a source of wave energy so as to maintain the desired configuration.

It is a further object of the present invention to provide an improved method and means for shaping an article into a desired configuration and thereafter immobilizing the article without impregnating the surface of the article with a stiffening agent which is sticky or malodorous.

It is still another object of the present invention to provide an improved pliable or flexible fabric which can be immobilized on exposure to wave energy without having the fabric impregnated with a stiffening agent such that the fibers forming the fabric have the stiffening agent in surrounding relationship therewith.

It is a still further object of the present invention to provide an improved spun plastic flexible, pliable or elastic filament or tubule which is adapted to be immobilized on exposure to a suitable source of wave energy without having a stiffening agent exposed on the surface of the filament or tubule.

It is still another object of the present invention to provide an improved method and means for forming in situ an orthopedic cast or support member which can be immobilized on exposure to wave energy.

It is still further an object of the present invention to provide an improved plastic orthopedic cast or like body support device which permits improved air circulation and breathing of the cast.

Other objects of the present invention will be apparent to one skilled in the art from the detailed description and claims to follow when read in conjunction with the accompanying drawing, wherein:

FIG. 1 is an enlarged cross-sectional view of an elongated flexible, pliable or elastic element embodying the present invention;

FIG. 2 is an enlarged cross-sectional view of the element of FIG. 1 in a rigid immobilized form;

FIG. 3 is a cross-sectional view of a modified form of an elongated flexible, pliable or elastic element embodying the present invention;

FIG. 4 is a cross-sectional view of a still further modified form of an elongated flexible, pliable or elastic element embodying the present invention;

FIG. 5 is a diagrammatic perspective view of a further embodiment of the present invention comprising a pliable cylindrical fabric sleeve-like article formed from the element of FIG. 1;

FIG. 6 is a diagrammatic perspective view of the article of FIG. 5 applied to the wrist of a patient as an orthopedic cast; and FIG. 7 is a diagrammatic perspective view of a still further embodiment of the present invention showing a stockinette formed of the element of FIG. 1 applied to the foot and ankle of a patient.

The objects of the present invention are achieved by providing an elongated flexible, pliable or elastic element, such as a small diameter filament or tubule, which is comprised of a filament forming material, preferably of a high molecular weight organic composition, having enclosed entirely within the main body portion thereof and extending throughout the length thereof a polymerizable material which remains in a pliable or liquid state until exposed to ultra-violet light or other forms of radiant or wave energy and which is capable of being polymerized into a rigid form on exposure to ultra-violet light or other form of radiant or wave energy having a sufficient intensity to effect polymerization and thereby rigidifying the filament or tubule and any article or structure of which the filament is a part. More particularly, the elongated flexible, pliable or elastic element embodying the present invention preferably comprises an elongated small diameter spun filament which has a polymerizable organic material containing where required a sensitizing polymerization initiator protectively enclosed and retained entirely within the body of the spun filament. The polymerizable organic material can be enclosed within one or more longitudinally extending passages or spaced pockets formed in the spun filament. Thus, the fiber-like article can be a spun tube-like element having an axial passage extending longitudinally therethrough with the polymerizable organic material enclosed within the axial passage, or the elongated element can have a plurality of uniformly spaced longitudinally extending passages or pockets formed within a flexible, pliable or elastic small diameter rod-like body portion of the element with the polymerizable organic material protectively enclosed therein. The polymerizable organic material and the polymerization initiator can also be enclosed within a plurality of elongated randomly spaced passages or pockets formed within a spun tubular or rod-like member with the pockets being relatively short and distributed throughout the spun pliable plastic in overlapping spaced relationship within the wall of a tubular member or throughout the body of a rod-like member. The elongated flexible, pliable or elastic element or an article formed therefrom, after being shaped to the desired configuration, can be readily transformed into a rigid form by exposing the element or article to a suitable source of wave energy, preferably a source of ultra-violet light which effects polymerization.

In one preferred embodiment of the present invention as shown in FIGS. 1 and 2, a high molecular weight organic composition is extruded through a composite spinning head (not shown) to form a flexible, pliable or elastic small diameter filament or tubule 10 comprised of a flexible, pliable or elastic cylindrical outer sheath or wall section 11 and a lumen or core portion 12 which is filled with a pliable or liquid polymerizable organic material 13 having where required a photosensitizing polymerization initiator mixed therewith which is adapted to be transformed by polymerization into a rigid core 14 (see FIG. 2) when the filament is exposed to an appropriate source of ultra-violet light. The filament and tubules which can be used in the present invention preferably have a diameter ranging between about 0.001 inches and 0.200 inches. Spinning nozzles suitable for making flexible, pliable or elastic filaments having the foregoing structures are well known in the textile fiber spinning art, and one such multiple-hole spinning nozzle is shown in U.S. Pat. No. 3,075,241. A spinneret for forming fibers having a centered core is also shown in U.S. Pat. No. 3,458,615.

While the foregoing fiber-like filaments or tubules are capable of being used directly as packaging material for immobilizing the contents of a container during transport by exposing the tubules to ultra-violet light after the filaments or tubules supportively contact an article within the container, a particularly useful application of the foregoing filaments or tubules comprises interlacing one or more of the flexible, pliable or elastic filaments or tubules, as by knitting, weaving or felting, to provide a fabric in the form of an elongated strip, sleeve, stockinette, glove, body stocking or like stretchable and form-fitting article of wearing apparel. The article formed preferably has a considerable degree of elasticity which can be obtained from the type of the interlacing used to form the fabric or the elastic properties of the spun fibers themselves, so that the article when applied to the body member or other structure will conform generally to the contours thereof and, after being transformed into its substantially rigid form, will provide a light weight, water proof, attractive orthopedic cast, brace or splint which will effectively immobilize a body fracture or provide the desired support for a structure in contact therewith.

FIG. 3 shows a modified form of the invention in which the flexible, pliable or elastic small diameter filament 15 has an extruded rod-like body section 16 with a plurality of uniformly spaced longitudinally extending passages or pockets 17 which are filled with a liquid or pliable polymerizable organic material 18.

FIG. 4 shows a further modified form of the invention in which the flexible, pliable or elastic small diameter filament 20 has an extruded rod-like body section 21 with a plurality of randomly spaced passages or pockets 22 enclosed within the body section 21 and filled with a liquid or pliable polymerizable organic material 23 which is readily polymerizable to a rigid solid on exposure to a source of wave energy, such as ultra-violet light.

FIGS. 5 and 6 of the drawing illustrate an embodiment of the present invention wherein a cylindrical fabric sleeve 30 is formed so as to have elastic properties by interlacing, preferably by knitting, a plurality of the flexible, pliable or elastic tubular elements 10 of FIG. 1 before exposing the elements 10 to ultra-violet light. The elastic properties are provided by the type of the interlacing used in forming the sleeve 30 or the elastic properties of the tubular element per se. In use the sleeve 30 can be placed over a patient's hand and wrist 31 so that it conforms generally to the shape of the hand and wrist (see FIG. 6). When the sleeve 30 is exposed to ultra-violet light, the liquid or pliable core material 13 within the tubular elements 10 is transformed into a rigid core 14 as a result of the polymerization reaction initiated by exposing the sleeve 30 to the ultra-violet light. The tubular elements 10 after polymerization is complete are mechanically interlocked to form a rigid, lightweight, waterproof cast on the patient's wrist and hand.

FIG. 7 illustrates a sock-like article 35 formed by interlacing, preferably by knitting, the flexible, pliable or elastic tubular element 10 of FIG. 1. The stockinette, being resilient prior to exposure to ultra-violet light, is readily placed over a patient's ankle and foot 36. When exposed to ultra-violet light the liquid or pliable core material 13 within the tubular elements 10 is polymerized into a rigid form causing the tubular elements to mechanically interlock and providing a rigid, lightweight, waterproof cast for the patient's ankle and foot without the outer surfaces of the tubular elements 10 being bonded together.

In addition to providing pliable articles for the foregoing type, the flexible, pliable or elastic filaments of the present invention can be interlaced in any desired manner to provide an elongated strip of fabric similar to an elastic bandage which can be applied to a body member or other article by wrapping in overlapping relationship and thereafter exposing to a source of radiant or wave energy to form a rigid support for the body member or other article. Effective splints and braces can also be made by providing a tubular structure which has only a part of a circumference thereof formed of the flexible, pliable or elastic filament of the present invention with the remainder of the circumference comprised of an elastic type strip or other suitable material.

The filament or tubular article of the present invention can also be used by interlacing, with or without other types of filaments of fibers, so as to provide a woven or non-woven pliable fabric which can be used for custom packaging, making industrial shields, shoe liners, automobile body patch work, fiber glass patch work, sculpture material, angel hair and other decorating material, space-station shields which can be easily folded and stowed aboard a space ship and which become structurally strong after being unfolded and exposed to ultra-violet light, making durable press collars or cuffs and other wearing apparel, quick setting sheet-like material which can be draped over a mold and immediately hardened, tents and other protective enclosures, and patching material for conduits and the like, which becomes structurally strong after being erected and exposed to sunlight or other source of radiant energy as a result of the filaments or tubules being rigidified and mechanically interlocked when the incompletely polymerized material within the interior of the filament is completely polymerized.

The flexible, pliable or elastic elements of the present invention can have one or more other materials used therewith which impart special properties to the elements, such as a coloring agent or a fire retarding substance incorporated in the high molecular weight organic composition or in the polymerizable material or even applied as a coating on the surface of the flexible element, depending on the energy transmitting or absorption qualities of the coating material and the nature of the energy source.

The organic materials which are considered particularly useful for spinning the outer cylindrical sheath portion of a tubular element and the main body portion of a rod-like element are the high molecular weight organic compositions including but not limited to cellulose, cellulose compounds, and especially the synthetic resins comprising vinyl, acrylic, olefin, amide, ester, ether, siloxane, urethane, and other known functional groups, including but not limited to the class of materials generally known as elastomers, particularly modern linear polymers, which are capable of being transformed into flexible, pliable or elastic solids by methods well known in the textile synthetic fiber art. The composition used in each instance must permit passage of the wave energy used to effect polymerization of the core material while being impermeable to the liquid or pliable core material within the spun element.

The method chosen to produce the filaments or tubules of the present invention depends on the nature of the synthetic resin which is used. Melt spinning is appropriate for olefin, amide, ester, and other polymers which can be melted and extruded, without deleterious thermal degradation. Dry spinning, which results in fiber formation by evaporation of solvent from a solution of resin, and wet spinning, which results in fiber formation by physical or chemical interaction of coagulant with a solution of resin, are appropriate for those resins that are stable as solutions but unstable as melts. Combinations of these methods are also known and may be used to advantage to maintain the desired shape of the extruded tubular element, as in the melt spinning of a resin which contains plasticizer or volatile melting-point depressant, or in the dry spinning of a resin solution into a coagulation bath. The latter process, which is called "gap spinning", is particularly useful for resins which may be dry spun or wet spun from the same solution.

The polymerizable materials which are capable of being transformed from the pliable or liquid incompletely polymerized state to the rigid highly polymerized state on exposure to radiant or wave energy, include but are not limited to the polymerizable organic compounds having a photosensitive initiator admixed therewith, as taught in U.S. Pat. Nos. 2,413,973; 3,326,710 (and patents cited therein), 3,613,675; 3,421,501 and 3,649,724, and the teaching of these patents are incorporated by reference herein.

It should be understood, however, that the present invention is not limited to the use of a polymerizable organic material which can be polymerized by exposure to a source of ultra-violet light or radiant energy, as other polymerizable organic compositions can be used, including compositions which can be polymerized by ultrasonic energy, such as disclosed in U.S. Pat. No. 3,618,599. Compositions which are polymerizable by radio frequency waves as taught in U.S. Pat. No. 2,871,911 can also be used as the polymerizable material enclosed within the elongated flexible element of the present invention. Where it is not objectionable, polymerization can be effected by a degree of heating. Thus, included among the polymerizable organic compositions which can be used in the present invention are compositions which are polymerizable by exposure to infra-red rays, x-rays, atomic radiation, gamma rays, or other forms of radiant or wave energy. And, in some of the embodiments of the present invention it is not necessary to use polymerization initiator, as where exposure to heat, radiation or other forms of wave energy is sufficient to cause polymerization in the absence of a polymerization initiator.

It should also be understood that the herein disclosed elongated flexible, pliable or resilient elements containing a polymerizable organic material can be combined with one or more other natural or synthetic fibers, filaments or elongated tubular members where special properties are required.

By way of further exemplifying the present invention two extruded flexible tubular members were formed, one having an outer diameter of 0.047 inches and an inner diameter of 0.025 inches and the other having an outer diameter of 0.077 inches and the inner diameter of 0.058 inches using Silastic plastic material (a silicone produced by Dow-Corning of Midland, Michigan) and having the core portion filled with a polymerizable organic material comprising an isocyanate modified bisphenol A glycidyl methacrylate co-monomer blend (No. H3/18/5, Batch 73260-manufactured by the L. D. Caulk Company of Milford, Delaware), and containing admixed therein as the photosensitizing polymerization initiator, a 2 percent solution of benzoin methyl ether in dibutyl sebacate. In the co-monomer blend both the main resin and the diluent monomer which was used to control viscosity were di-functional. One drop of the initiator was used for each gram of the co-monomer. Whereas before exposure to ultra-violet radiation each of the above tubular members (both the individual elements and when interlaced) containing the polymerizable co-monomer mixture in the core portion thereof were very flexible, the individual tubular members and the interlaced tubular members exhibited a very rigid structure without any surface bonding between the tubular members after a two minute exposure to an ultra-violet light source which consisted of a Hanovia No. 679A high pressure Mercury vapor lamp with a total radiated energy of 175.8 watts over a wavelength region from 220 mm to 1400 mm at a distance of two inches.

Tubular elements or filaments containing photopolymerizable liquid in the core thereof in accordance with the present invention were spun by metering a photopolymerizable liquid into the center of a stream of molten polymer immediately before the molten polymer passed through the orifice of a spinneret. The photopolymerizable liquid was prepared by adding 20 drops of a photosensitizing polymerization initiator consisting of a 2 percent solution of benzoin methyl ether in dibutyl sebacate (H3-53-3, The L. D. Caulk Co.) to 20 g of an isocyanate modified bisphenol A glycidyl methacrylate co-monomer blend (H4-37-IC, The L. D. Caulk Co.) in an amber bottle, and heating the bottle and contents at 50° C in an ultrasonic bath for 30 minutes to remove entrapped air. The main resin in the blend was di-functional and the diluent monomer used to control viscosity was tri-functional. The liquid photopolymerizable mixture, which was stored overnight in the dark at room temperature before use, was placed in the smaller of two feed cylinders for pumping into the spinning device, and polyethylene resin (DMDA 8925Nt7, Union Carbide Corp.) was placed in the larger cylinder which had been heated to 140° C. The molten polyethylene and the photopolymerizable liquid were pumped through the orifice at rates of about 0.7 to 1.3 g/min, and the resulting filaments, which were tubes filled with the liquid photopolymerizable material, were collected at take-up speeds of 9 to 16 feet/min by a surface-driven winder 4 feet below the spinneret. The sample which was collected at 16 feet/min, had a lumen diameter of 0.014 in. and an outer diameter of 0.02. The sample which was collected at 9 feet/min. had a lumen diameter of 0.022 inches and an outer diameter of 0.03 inches.

Portions of each sample were wound around 13-mm glass tubes and exposed to ultraviolet light for ten minutes at a distance of six inches from a 200-watt, Hanovia Model S highpressure mercury-vapor lamp. Before exposure the samples were soft and very flexible; after exposure both test samples were hard and rigid.

The terms "spinning" and "spun" as used in the specification and claims are intended to denote the all embracing principle of the plastic working or shaping of material under pressure or tension and in addition to their narrow technical sense comprise also the process of extrusion pressing or drawing, of injection molding and of pressure casting and the like.

The term "wave energy" as used in the specification and claims designates all forms of energy which are radiated or propagated through space by wave or impulse including but not limited to ultraviolet light, x-rays, atomic radiation, gamma rays, sonic waves, radio waves and heat waves.

We claim:

1. An article of manufacture comprising a pliable fabric having at least one interlaced elongated flexible element, such as a small diameter filament or tubule, having the body portion of said element formed of a high molecular weight organic composition and having protectively enclosed and retained entirely within said body portion a polymerizable organic material in a pliable form which when exposed to a source of wave energy which has an intensity effecting polymerization of said polymerizable organic material is transformed to a rigid form and rigidifies the said flexible element and said fabric without having the interstices of said interlaced elongated flexible element comprising said fabric impregnated with said polymerizable organic material, and said fabric characterized by being formable into a desired configuration before exposure to said wave energy and while thus formed being transformable into a rigid form corresponding to said configuration on exposure to a said source of wave energy.

2. An article as in claim 1, wherein the said elongated element has at least one longitudinally extending enclosure formed within said body which retains therein said polymerizable organic material.

3. An article as in claim 2, wherein said longitudinally extending enclosure is an axial passage extending lengthwise of said element.

4. An article as in claim 1, wherein said elongated element has said polymerizable organic material distributed along the length and across the width thereof in a plurality of spaced longitudinally extending enclosures formed within said body of said element.

5. An article as in claim 1, wherein said fabric has the said elements interlaced to form a knit fabric.

6. An article as in claim 1, wherein said fabric has the said elements interlaced to form a woven fabric.

7. An article as in claim 1, wherein said fabric has the said elements interlaced to form a felted fabric.

8. An article as in claim 1, wherein said fabric is interlaced to provide elastic properties and is adapted to yieldably engage a body member when placed in surrounding contact therewith.

9. An article as in claim 1, wherein the said body of the elongated flexible element is adapted to transmit ultra-violet light therethrough, and said source of wave energy is a source of ultra-violet light.

10. An article as in claim 1, wherein said elongated flexible element is a spun filament having an exterior diameter between about 0.001 inches and 0.200 inches.

11. A pliable fabric which is rigidifiable comprising at least one interlaced elongated small diameter flexible filament having a main body portion formed of a high molecular weight organic composition through which ultra-violet radiation passes, said filament having a photopolymerizable organic composition in a pliable form protectively enclosed and retained entirely within its body portion throughout the length thereof in at least one longitudinally extending passage, said photopolymerizable composition being polymerizable to a rigid form which effects rigidifying the said filament on exposure thereof to ultraviolet radiation without having the interstices of said interlaced elongated flexible element forming said fabric impregnated with said polymerizable organic material, and said fabric characterized by being formable into a select configuration prior to exposure to said ultra-violet radiation and being rigidly held in said configuration on exposure of said fabric to said ultra-violet radiation.

12. A pliable fabric as in claim 11, wherein said photopolymerizable organic composition contains a photosensitizing polymerization initiator which is activated on exposure to said ultra-violet radiation.

13. A pliable fabric as in claim 11, wherein said filament is interlaced to form a fabric sleeve structure having elastic properties which impart stretchability and form-engaging characteristics to the fabric sleeve structure.

14. A pliable fabric as in claim 13, wherein said fabric sleeve has the general configuration of a portion of a body of a human which enables said sleeve to be mounted on a portion of said body; whereby said sleeve after mounting on said body portion forms a rigid support for the said bodily portion on exposure of said sleeve to said ultra-violet radiation.

* * * * *